United States Patent [19]

RajBhandary

[11] Patent Number: 5,879,905
[45] Date of Patent: Mar. 9, 1999

[54] IN VIVO METHOD OF INITIATING PROTEIN SYNTHESIS WITH AN AMINO ACID OTHER THAN METHIONINE

[75] Inventor: Uttam L. RajBhandary, Lexington, Mass.

[73] Assignee: Massachusetts Institute of Technology, Cambridge, Mass.

[21] Appl. No.: 705,196

[22] Filed: Aug. 29, 1996

[51] Int. Cl.$^6$ .............................. C12P 21/06; C12P 21/04; C12N 15/00

[52] U.S. Cl. .................... 435/69.1; 435/69.6; 435/172.3; 435/71.1; 435/71.2

[58] Field of Search ................................ 435/172.3, 69.1, 435/69.6, 71.1, 71.2

[56] References Cited

U.S. PATENT DOCUMENTS 5,268,284  12/1993  Tomich et al. ....................... 435/172.3

OTHER PUBLICATIONS

Wu, Xin–Qi, et al., "Ribosome–Initiator tRNA Complex as an Intermediate in Translation Initiation in *Escherichia coli* Revealed by Use of Mutant Initiator tRNAs and Specialized Ribosomes", *The EMBO Journal*, 15(17):4734–4739 (1996).

Hoffman, Stephen J., et al., "Expression of Fully Functional Tetrameric Human Hemoglobin in *Escherichia coli*", *Proc. Natl. Acad. Sci. USA*, 87:8521–8525 (1990).

Olson, Kenneth C., et al., "Purified Human Growth Hormone From *E. coli* is Biologically Active," *Nature*, 293(5831):408–411 (1981).

Mangroo, D. et al., *Escherichia coli* Initiator tRNA: Structure–function Relationships and Interactions with the Translational Machinery, *Biochem. Cell Biol.*, 73:1023–1031 (1995).

Mangroo, D. and RajBhandary, U., "Mutants of *Escherichia coli* Initiator tRNA Defective in Initiation", *J. Biol. Chem.*, 270:12203–12209 (1995).

Varshavsky, A. et al., "The N–End Rule of Selective Protein Turnover" in *Ubiquitin*, M. Rechsteiner (Ed.), Plenum Publishing Corp., 1988.

Giege, R. et al., "Formylation of Mischarged *E. coli* tRNA$_f^{Met}$", *FEBS Letters*, 30(3):291–295 (1973).

Giege, R. et al., "Initiation of Protein Synthesis With Mischarged tRNA$_f^{Met}$ From *E. coli*", *FEBS Letters*, 37(2):166–169 (1973).

Brown, J.L., "The Modification of the Amino Terminal Region of *Escherichia coli* Proteins After Initiation With Methionine Analogues", *Biochem. Biophys. Acta*, 294(3):527–629 (1973).

Mertes, M. et al., "Isoleucylation of Transfer RNA$_f^{Met}$ (*E. coli*) by Isoleucyl–Transfer RNA Synthetase from *Escherichia coli*", *J. Mol. Biol.*, 71:671–684 (1972).

Cigan, A.M. et al., "tRNA$_i^{Met}$ Functions in Directing the Scanning Ribosome to the Start Site of Translation", *Science*, 242:93–97 (1988).

Schulman, L.H. and Pelka, H., "In Vitro Conversion of a Methionine to a Glutamine–Acceptor tRNA", *Biochemistry*, 24:7309–7314 (1985).

Schulman, L.H. and Pelka, H., "Anticodon Loop Size and Sequence Requirements for Recognition of Formylmethionine tRNA by Methionyl–tRNA Synthetase", *Proc. Natl. Acad. Sci., USA*, 80:6755–6759 (1983).

Schulman, L.H. and Abelson, J., "Recent Excitement in Understanding Transfer RNA Identity", *Science*, 240:1591–1592 (1988).

Normanly, J. and Abelson, J., "tRNA Identity", *Annu. Rev. Biochem.*, 58:1029–1049 (1989).

RajBhandary, U.L., "Modified Bases and Aminocylation", *Nature*, 336:112–113 (1988).

Muramatsu, T. et al., "Codon and Amino–Acid Specificities of a Transfer RNA Are Both Converted by a Single Post–Transcriptional Modification", *Nature*, 336:179–181 (1988).

Schulman, L.H. et al., "The Role of the Anticon in the Identity of *E. coli* tRNAs", Abstract, 13th International tRNA Workshop, Vancouver, B.C. Jun. 4–9, 1989.

Schulman, L.H. and Pelka, H., "Anticodon Switching Changes the Identity of Methionine and Valine Transfer RNAs", *Science*, 242:765–768 (1988).

Schulman, L.H. and Pelka, H., "The Anticodon Contains a Major Element of the Identity of Arginine Transfer RNAs", *Science*, 246:1595–1597 (1989).

Schulman, L.H. and Pelka, H., "An Anticodon Change Switches the Identity of *E. coli* tRNA$_m^{Met}$ From Methionine to Threonine", *Nucl. Acids Res.*, 18(2):285–289 (1990).

Chattapadhyay, R. et al., "Initiation of In Vivo Protein Synthesis with Non–Methionine Amino Acids", *Biochemistry*, 29(18):4263–4278 (1990).

Seong, B.L. et al., "Suppression of Amber Codons in Vivo as Evidence That Mutants Derived From *Escherichia coli* Initiator tRNA Can Act at the Step of Elongation in Protein Synthesis", *J. Biol. Chem.*, 246(11):6504–6508 (1989).

Varshney, U. and RajBhandary, U.L., "Initiation of Protein Synthesis From a Termination Codon", *Proc. Natl. Acad. Sci., USA*, 87:1586–1590 (1990).

Sampson, J.R. et al., "Nucleotides in Yeast tRNA$^{Phe}$ Required for the Specific Recognition by Its Cognate Synthetase", *Science*, 243:1363–1366 (1989).

Sherman, F. et al., "Methionine or Not Methionine at the Beginning of a Protein", *Bioessays*, 3(1):27–32 (1985).

Huang, S. et al., "Specificity of Cotranslational Amino–Terminal Processing of Proteins in Yeast", *Biochemistry*, 26:8242–8246 (1987).

Biossel, J.–P. et al., "Cotranslational Amino–Terminal Processing of Cytosolic Proteins", *J. Biol. Chem.*, 263(17):8443–8449 (1988).

(List continued on next page.)

*Primary Examiner*—Jasemine C. Chambers
*Assistant Examiner*—Deborah J. R. Clark
*Attorney, Agent, or Firm*—Hamilton, Brook, Smith & Reynolds, P.C.

[57] ABSTRACT

A method of overproducing proteins which are initiated with an amino acid other than methionine, in which methionyl-tRNA transformylase and, optionally, the appropriate tRNA synthetase are overexpressed in a host cell.

9 Claims, 2 Drawing Sheets

OTHER PUBLICATIONS

Hirel, Ph.–H. et al., "Extent of N–terminal Methionine Excision From *Escherichia coli* Proteins Is Governed by the Side–Chain Length of the Penultimate Amino Acid", *Proc. Natl. Acad. Sci., USA,* 86:8247–8251 (1989).

Bachmair, A. et al., "In Vivo Half–Life of a Protein is a Function of Its Amino–Terminal Residue", *Science,* 234:179–186 (1986).

Bachmair, A. and Varshavsky, A., "Degradation Signal in a Short–Lived Protein", *Cell,* 56: 1019–1032 (1989).

Gonda, D.K. et al., "Universality and Structure of the N–End Rule", *J. Biol. Chem.,* 264(28):16700–16712 (1989).

Pallanck, L. and Schulman, L.H., "Anticodon–dependent Aminoacylation of a Noncognate tRNA with Isoleucine, Valine, and Phenylalanine in vivo", *Proc. Natl. Acad. Sci., USA,* 88:3872–3876 (1991).

Orkin et al. Report and recommendations of the panel to assess the NIH investment in research on gene therapy, Dec. 7, 1995.

Varshney et al. Role of methionine and formylation of initiator tRNA in initiation of protein synthesis in *E. coli.* J. of Bacteriology, vol. 174, No. 23, pp. 7819–7826, Dec. 1992.

Li et al. Important Role of the Amino Acid Attached to tRNA in Formylation and in Initiation of Protein Synthesis in *Escherichia coli.* J. of Biological Chemistry, vol. 271, No. 2, pp. 1022–1028, Jan. 12, 1996.

CAT2.5    ...UUUCAGGAGCUAAGGAAGCUAAAAUGGACAAAAAAACCACU...

CATV1.2.5 ...UUUCAGGAGCUAAGGAAGCUAAAGUCGACAAAAAAACCACU...

CATI1.2.5 ...UUUCAGGAGCUAAGGAAGCUAAAAUCGACAAAAAAACCACU...

IN VIVO METHOD OF INITIATING PROTEIN SYNTHESIS WITH AN AMINO ACID OTHER THAN METHIONINE

FUNDING

Work described herein was funded by Grant GM17151 from the National Institutes of General Medical Sciences, NIH.

BACKGROUND OF THE INVENTION

Methionine is the only naturally occurring amino acid known to initiate protein synthesis (Lucas-Lenard, J. and F. Lipmann, *Ann. Rev. Biochem.*, 40:409–448 (1971)). In prokaryotes, the amino acid is first attached to the initiator methionine tRNA by methionyl-tRNA synthetase and subsequently formylated by methionyl-tRNA transformylase. The resulting f-Met-tRNA$^{fMet}$ initiates protein synthesis in a reaction dependent on initiation factor 2 (IF-2).

Aminoacylation of *E. coli* methionine tRNAs depends on recognition of the methionine anticodon CAU by *E. coli* methionyl-tRNA synthetase (Schulman, L. H. and H. Pelka, *Proc. Natl. Acad. Sci., USA,* 80:6755–6759 (1983)). Mutations in this sequence lead to loss of methionine acceptor activity and, in some cases, to acquisition of a new amino acid acceptor activity corresponding to that of the altered anticodon sequence (Schulman, L. H. and H. Pelka, *Biochemistry,* 24:7309–7314 (1985); Schulman, L. H. and H. Pelka, *Science,* 242:765–768 (1988); Schulman, L. H. and H. Pelka, Science, 246:1595–1597 (1989); Schulman L. H. and H. Pelka, *Nucleic Acids Res.,* in press (1990).

SUMMARY OF THE INVENTION

The present invention relates to an in vivo method of overproducing, in an appropriate host cell (e.g., a bacterium, such as *E. coli*), a protein which is initiated with an amino acid other than methionine (a protein in which the amino terminal amino acid is other than methionine). In the method, a host cell is modified by the introduction, using known methods (e.g., transformation, transfection, infection), of: a) DNA which encodes the protein to be produced and which comprises an initiator codon for an amino acid other than methionine; b) DNA which encodes a mutant initiator tRNA containing the corresponding anti-codon (for the initiation codon of the DNA which encodes the protein to be produced); and c) DNA encoding methionyl-tRNA transformylase. The resulting modified host cells are maintained under conditions appropriate for overproduction of the methionyl-tRNA transformylase (MTF) and expression of the DNA which encodes the protein to be produced (the protein in which the amino terminal amino acid is other than methionine). As a result, the protein which is initiated with an amino acid other than methionine is overproduced. Optionally, DNA encoding the appropriate aminoacyl tRNA synthetase (which is determined by the amino acid with which the protein is initiated) is also introduced into and produced (overproduced) in the host cell. In a particular embodiment of the invention, the protein produced is initiated with valine, isoleucine or phenylalanine. The present method may be used to produce proteins with therapeutic and diagnostic applications, such as hemoglobin and somatotropin. Proteins produced by the claimed method are also the subject of the invention.

DETAILED DESCRIPTION OF THE INVENTION

Figure 1B:
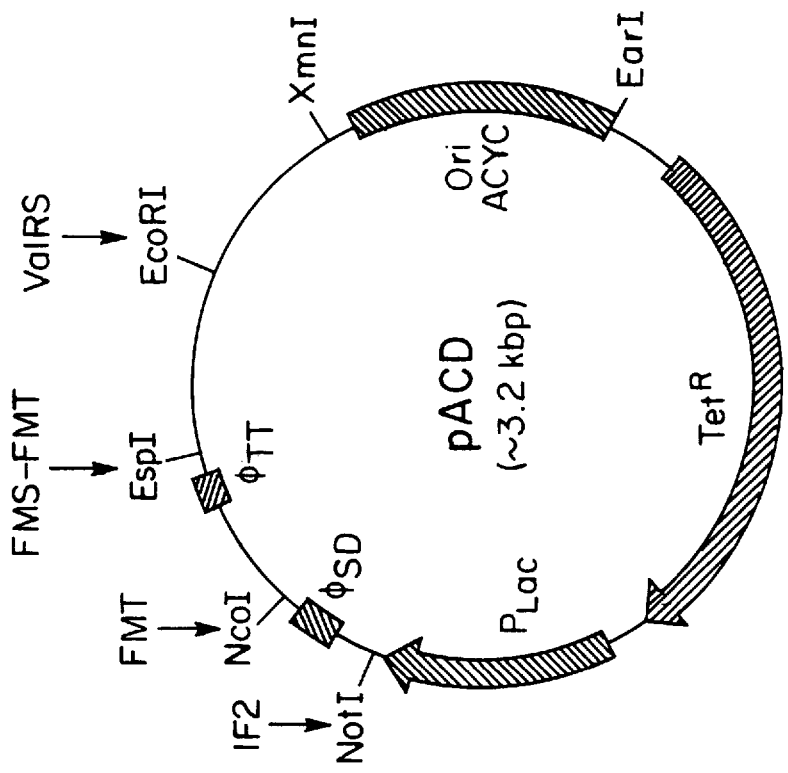
FIG. 1B shows the plasmids used for expression of the IF2, FMT or FMS-FMT genes (encoding FMT) and ValRS gene. Vertical arrows indicate the sites on the PACD vector used for cloning of the various genes.

The present invention relates to an in vivo method of producing proteins which are initiated with (have as their amino terminal amino acid) an amino acid other than methionine. It has now been shown that proteins which include an amino acid other than methionine can be overproduced in host cells which contain DNA which encodes a protein to be produced and has an initiation codon for an amino acid other than methionine (a non-methionine initiator codon); a mutant initiator tRNA which contains the corresponding anti-codon sequence; DNA encoding methionyl-tRNA transformylase (MTF), which is overexpressed in the host cells; and, optionally, DNA encoding the appropriate aminoacyl tRNA synthetase for the protein being produced. Work described herein shows that in host cells in which MTF is overexpressed (produced at higher levels than it is produced in the normal host cell, which contains a single copy of the MTF-encoding gene), a protein initiated with an amino acid other than methionine is overexpressed. In particular, it has been shown that protein initiated with valine or isoleucine is overproduced in host cells (e.g., *E. coli*) in which MTF is overexpressed and that, in the case of protein initiated with valine, production is further enhanced when the appropriate aminoacyl tRNA synthetase (ValRS) is also expressed in the host cells.

Described herein is an assessment of whether mutant initiator tRNAs which read initiation codons other than the methionine initiation codon produce more of a selected protein which is initiated with an amino acid other than methionine in vivo than the combination of the wild-type initiator tRNA and the corresponding wild-type gene and results of that work. Also described are two mutant initiator tRNAs with the anticodons GAC and GAU and two corresponding gene mutants with the initiation codons GUC and AUC, respectively. As described herein, these mutant initiator tRNA/mutant selected gene combinations produce more of the encoded protein than the wild-type initiator tRNA/wild-type gene combination. In particular, Applicant has shown that a protein initiated with valine or isoleucine is produced at enhanced levels in *E. coli* in which MTF is overexpressed, alone or in combination with expression of the appropriate aminoacyl tRNA synthetase.

The present invention relates to an in vivo method of initiating protein synthesis with an amino acid other than methionine and to an in vivo method of enhanced production (referred to as overproduction) of proteins in which protein synthesis is initiated with an amino acid other than methionine, with the result that the protein product has, at its amino terminal end, an amino acid other than methionine. The amino terminal amino acid can be any of the 19 other naturally-occurring amino acids. In specific embodiments, production of proteins which are initiated with isoleucine, valine or phenylalanine is enhanced, resulting in proteins which contain, respectively, an amino terminal isoleucine, valine or phenylalanine. The present invention further relates to the proteins overproduced, which contain an amino acid other than methionine (e.g., isoleucine, valine or phenylalanine) at the amino terminal end. In addition, the invention relates to an in vivo method of producing proteins which are normally toxic to host cells in which they are produced. In specific embodiments, the method of the present invention may be used to produce hemoglobin (in which the amino terminal amino acid is valine), human or porcine somatotropin (in which the amino terminal amino acid is valine) or any protein which is initiated with valine, isoleucine or phenylalanine.

The in vivo method of enhanced production of a protein with an amino terminal amino acid other than methionine is carried out as described below: the following are introduced into an appropriate host cell, which can be a prokaryote or a eukaryote: a) DNA which encodes the protein and which has an initiator codon for other than methionine (a nonmethionine initiator codon); b) DNA encoding a mutant initiator tRNA containing the corresponding anticodon sequence; and c) DNA encoding methionyl-tRNA transformylase (MTF). In one embodiment, in addition to a)–c) above, DNA encoding the appropriate aminoacyl tRNA synthetase is introduced into host cells. DNA encoding MTF is introduced into host cells in a vector which results in overexpression of MTF in recipients. In the embodiment in which MTF and the appropriate aminoacyl tRNA synthetase are expressed in host cells, the DNA encoding MTF and the DNA encoding the appropriate aminoacyl tRNA synthetase are introduced into host cells in a vector or vectors which result(s) in sufficient levels of expression of both the MTF and the appropriate aminoacyl tRNA synthetase. The resulting modified host cells (which now contain the DNA of a) and b) above, the mutant initiator tRNA and, optionally, DNA encoding the appropriate amino acid tRNA synthetase are maintained under conditions appropriate for overproduction of the MTF and, optionally, overproduction of the appropriate tRNA synthetase and synthesis of the protein to be produced. The resulting protein is obtained from the cells using known methods.

As a result of the method described herein, not only is it possible to produce proteins which are initiated with an amino acid other than methionine, but it is also possible to enhance their production (i.e., to achieve production of greater quantities of the desired protein than is possible when MTF or MTF and the appropriate aminoacyl tRNA synthetase are not overexpressed). As used herein, enhanced production of a protein refers to production of the protein at levels at least two-fold, preferably three-fold and even more preferably 5- or 6-fold higher than the levels produced by control cells. Control cells are the same cell type. They carry the wild-type gene, which has a methionine initiator codon encoding the desired protein.

In a specific embodiment described herein, a protein of interest which is initiated with valine is overproduced in an appropriate host cell (e.g., *E. coli*) when MTF is overproduced, alone or in combination with overexpression of valyl tRNA synthetase (ValRS). In one embodiment, the protein of interest is hemoglobin. In another embodiment, the protein of interest which is overproduced is initiated with isoleucine, which is overproduced in an appropriate host cell (e.g., *E. coli*) when MTF is overproduced.

The present invention is illustrated by the following exemplification, which is not intended to be limiting in any way.

EXEMPLIFICATION

Materials and Methods

The following materials and methods were used in the work described below.

Plasmids and strains

Figure 1A:
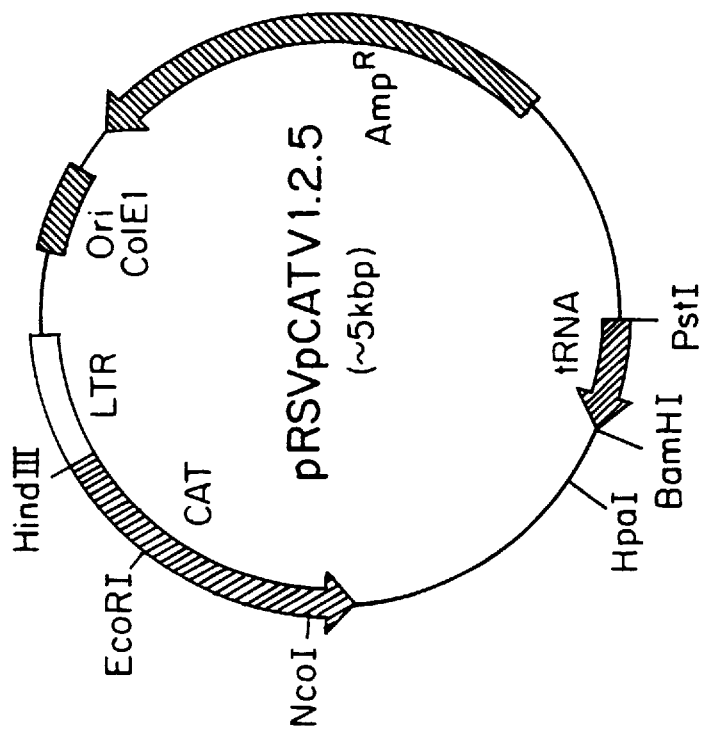
FIG. 1A shows the plasmids used for expression of CAT reporter gene and the initiator tRNA gene. The sites for cloning of the CAT gene and the tRNA gene are indicated by arrows.
Figures 2A, 2B:
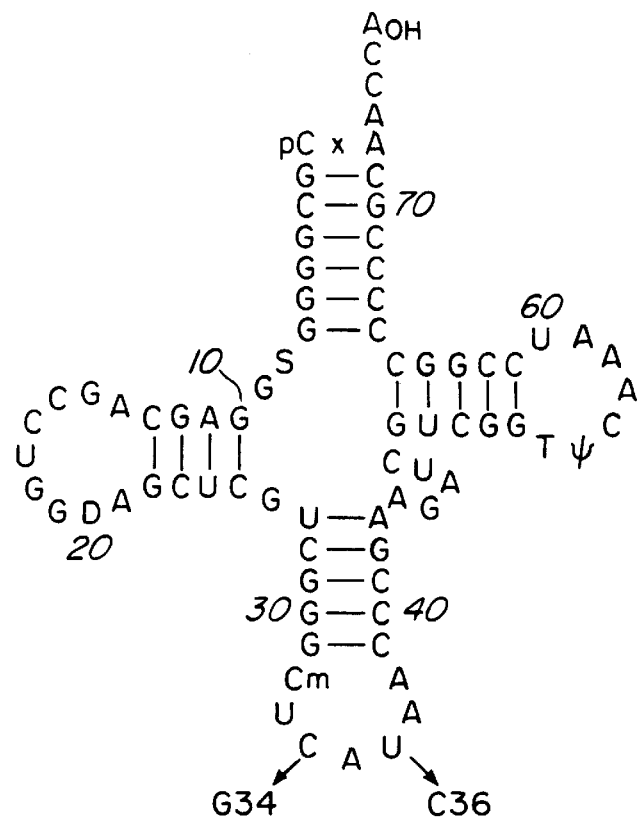
FIG. 2A shows the sites of mutation in the initiator tRNA$_2^{fMet}$. The two mutant tRNAs used are G34C36 and G34, have the anticodon sequence GAC and GAU, respectively, and are aminoacylated with valine and isoleucine, respectively.
FIG. 2B shows the initiation region of the CAT genes used. The CAT2.5 gene, which is referred to as the wild-type gene, has AUG as the initiation codon and changes in the second and the fifth codons that were introduced previously to remove weak secondary sites of initiation. The two mutants generated for this work are designated CATV1.2.5 and CATI1.2.5. These mutant CAT genes carry the same changes in the second and fifth codons as the CAT2.5 gene and have GUC and AUC, respectively, as the initiation codons.

The wild-type and the various mutant CAT reporter genes and the tRNA$^{fMet}$ genes were cloned into the plasmid pRSVp (Li et al., *J. Biol. Chem.*, 271:1022–1028 (1996); FIG. 1). The plasmid pACD (Mangroo and RajBhandary, *J. Biol. Chem.*, 270:12203–12209 (1995)) was used for overproduction of ValRS, IF2 and MTF. The ValRS, 1F2, FMT (coding for MTF and FMS-FMT genes (coding for peptidyl deformylase, which removes the formyl group from the N-terminus of proteins and MTF; Guillon et al., *J. Mol. Biol.*, 234:359–367 (1992)) were cloned into the EcoRI, Not1, Nco1 and Esp1 sites respectively (Mangroo and RajBhandary, *J. Biol. Chem.*, 270:12203–12209 (1995)). The FMS-FMT gene overproduced MTF more than the FMT gene alone and was used for overproduction of MTF in combination with overproduction of ValRS. The *E. coli* strain CA274 (hfrH LacZ125am trpEam) was used as the host cell for transformation with these plasmids (Smith and Cells, *Nature New Biol.*, 243:66–71 (1973)).

Mutagenesis

The mutagenesis characterization and subcloning of the mutant DNAs into the pRSVp vector were all as described before (Seong and RajBhandary, *Proc. Natl. Acad. Sci., USA*, 84:3343–338 (1987); Varshney and RajBhandary, *Proc. Natl. Acad. Sci., USA*, 87:1586–1590 (1990)).

Preparation of cell extracts for CAT and β-lactamase activity assays

Transformants of *E. coli* were grown overnight at 37° C. in 2X YT medium with ampicillin (100 μg/ml). The overnight culture was diluted 50- to 100-fold into 4 ml fresh 2X YT containing the same antibiotics and grown for another 4–6 hr. Cell extracts were prepared as described (Varshney et al., *J. Biol. Chem.*, 266:18018–18024 (1991)) and used for measurements of CT and β-lactamase activities. To minimize the effect of any possible variation in pRSVpCAT copy number in different transformants, the specific activity of CAT was normalized to the specific activity of β-lactamase in the same extract (Varshney et al., 1991b).

Immunoblot analysis of CAT and β-lactamase

An aliquot of the cell extracts containing 0.2 β-lactamase was used for SDS-polyacrylamide gel electrophoresis. The electrophoresis and transfer of proteins from gel to the immobilon membrane were as described (Varshney et al., *J. Biol. Chem.*, 1991b). For immunoblot analysis the ECL kit from Amersham Corp. was used.

Isolation and cloning of the *E. coli* ValRS gene

The ValRS gene was amplified from *E. coli* TGI chromosomal DNA by PCR. The primers used are based on the published gene sequence of ValRS (Hartlein et al., 1987) and are CGGAATTCTGCGAAACAAGCTTTGCAGA and ATGAATTCTTTACCATTTTGTATAAGAGA. The chromosomal DNA was prepared as described (Wilson, 1992). The mixture (50 μl) for PCR contained 0.5 μg genomic DNA, 50 mM KCl, 10 mM Tris-HCl, pH 9.0, 0.1% Triton X-100, 2.5 mM MgCl$_2$, 0.32 mM dNTP, 50 pmol each primer and 1 U Taq DNA polymerase. The amplification was done in a Perkin-Elmer thermoregulator through 1 cycle of incubation at 95° C. for 5 min, 55° C. for 40 s and 72° C. for 4 min, followed by 30 cycles of incubation at 94° C. for 1 min, 55° C. for 40 s and 72° C. for 4 min. The mixture was finally incubated for 10 min at 72° C. The ~3.2 kbp PCR product was digested with EcoRI (the VAlRS coding sequence does not have an EcoRI site) and cloned into the EcoRI site of the plasmid pACD (FIG. 1).

CAT activity in cells expressing the G34C36 mutant tRNA; effect of overproduction of IF2, ValRS, MTF and ValRS and MTF The Table shows the relative CAT activity in cells carrying the mutant initiator tRNA genes and the mutant CAT genes. Interestingly, CAT activity in cells carrying the G34G36 mutant initiator tRNA gene and the CATV1.2.5 gene is higher (approximately 1.6-fold) than in cells carrying the wild-type CAT gene. The CAT activity in cells carrying the CATV1.2.5 gene and the wild-type initiator tRNA gene on the same plasmid was <2% (data not shown). Therefore, translation of the CATV1.2.5 mRNA is dependent upon the presence of the corresponding G34G36 mutant initiator tRNA.

Overproduction of valyl-tRNA synthetase (ValRS), methionyl-tRNA transformylase (MTF) or both ValRS and MTF leads to further increases in CAT activity in cells carrying the G34G36 mutant initiator tRNA (Table). In cells overproducing ValRS alone, CAT activity goes up slightly. In cells overproducing MTF alone, CAT activity goes up approximately 2-fold. In cells overproducing both ValRS and MTF, CAT activity increases further, so that the relative CAT activity is now five to six times higher than in cells carrying the wild-type CAT gene. Overproduction of IF2 had little effect on CAT activity in cells carrying the G34G36 mutant initiator tRNA.

TABLE

Effect of overproduction of IF2 and MTF on relative CAT activities[a] in cells carrying the G34G36 and G34 mutant initiator tRNAs

| Initiator tRNA gene | CAT gene | Vector alone | IF2 | MTF | ValRS | ValRS + MTF |
|---|---|---|---|---|---|---|
| Wild-type | CAT2.5 | 100[b] | 65 | | 105 | 98 |
| G34G36 | CATV1.2.5 | 157 | 135 | 286 | 218 | 541 |
| G34 | CAI1.2.5 | 95 | 209 | 325 | | |

[a]The relative CAT activities shown are the average values in extracts of different clones and/or different cell extracts from the same clone.
[b]Relative CAT activity in extracts of cells carrying the wild-type CAT gene (CAT2.5), and overproducing the wild-type initiator tRNA is set at 100%.

Immunoblot analyses on cell extracts confirm the above results and show that the increased CAT activity in the various extracts is due to increased amounts of CAT protein. For example, while the levels of β-lactamase, another protein encoded in the same plasmid, are approximately the same across all lanes, there is much more of the CAT protein in some of the extracts compared with the others and the relative intensity of the bands corresponds to the relative CAT activities in the Table.

Effect of overproduction of ValRS, MTF and both ValRS and MTF on aminoacylation and formylation of the G34G36 mutant initiator tRNA in vivo.

Total tRNA isolated from CA274 transformants expressing the G34G36 mutant initiator tRNA was separated on an acid urea-polyacrylamide gel. The various forms of the mutant tRNA corresponding to the deacylated tRNA, aminoaaryl-tRNA and formylaminoacyl-tRNA were detected by Northern blot hybridization (Varshney et al., *J. Biol. Chem.*, 266:24712–24718 (1991)). A probe of the endogenous tRNA$^{Tyr}$ was used as an internal control. In cells not overproducing either ValRS or MTF, approximately 50% of the G34G36 mutant initiator tRNA is present as Val-tRNA (57%) and only approximately 20% is present as fAal-tRNA (based on phosphorimager analysis of the data). overproduction of MTF leads to conversion of all of the Val-tRNA to fVal-tRNA, whereas overproduction of both ValRS and MT leads to essentially complete conversion of the G34G36 mutant initiator tRNA to fVal-tRNA. Thus, there is a direct correlation between the effects of overproduction of ValRS, MTF and both ValRS and MTF on CAT activity in the cells on the one hand and levels of fVal-tRNA on the other.

As noted before, the endogenous tRNA$^{Tyr}$ is essentially all aminoacylated under all conditions (Varshney et al., *J. Biol. Chem.*, 266:24712–24718 (1991)).

CAT activity in cells expressing the G34 mutant tRNA

Similar experiments were done with the G34 mutant initiator tRNA and the CATI1.2.5 reporter gene. The table shows that CAT activity in extracts of cells expressing this tRNA and the CATI1.2.5 gene is about the same as that in cells expressing the wild-type CAT gene. However, overproduction of IF2 or MTF leads to a 2- or 3-fold increase, respectively, in CAT activity. Thus, as for the U35A36 and the G34G36 mutant initiator tRNAs, the combination of G34 mutant initiator tRNA and CATI1.2.5 gene produces more CAT protein than the combination of wild-type CAT gene and wild-type initiator tRNA gene. The results of immunoblot analyses of cell extracts are also in agreement with the results of CAT activity assays. Results of acid urea gel electrophoretic analysis of G34 mutant initiator tRNA shows that in cells overproducing MTF there is a substantial increase in levels of fIle-tRNA. This is in agreement with the data in the Table showing an increase in CAT activity in cells carrying the G34 mutant initiator tRNA and overproducing MTF. However, a substantial fraction (approximately 60%) of the G34 mutant initiator tRNA is still uncharged in vivo (based on phosphorimager analysis of a Northern blot; data not shown), suggesting that this tRNA is a poor substrate for isoleucyl-tRNA synthetase (IleRS). These results imply that the relative CAT activity of 325% in cells expressing the G34 mutant initiator tRNA and overproducing MTF (the Table) could be increased even more if the tRNA could be completely converted to fIle-tRNA by overproducing both IleRS and MTF.

Work described in this Exemplification shows that mutant CAT genes with GUC and AUC initiation codons produce more CAT protein in *E. coli* in the presence of the corresponding mutant initiator tRNAs than the CAT gene with an AUG initiation codon (the Table). These results demonstrate that the increased production of CAT protein from a mutant CAT mRNA mutant initiator tRNA combination compared with wild-type CAT mRNA/wild-type initiator tRNA combination is a general phenomenon and that proteins carrying amino acids other than methionine at their N-termini can be overproduced in *E. coli*

The conditions necessary for increased production of CAT protein in vivo depend upon the mutant initiator tRNA used. (i) With the G34G36 mutant, which is aminoacylated with valine, overproduction of IF2 had no effect. However, overproduction of ValRS and MTF increases greatly the synthesis of CAT protein (the Table). This is because the G34G36 mutant tRNA is a poor substrate for ValRS. Also, tRNA aminoacylated with valine is a poor substrate for MTF compared with tRNA aminoacylated with methionine (Giege et al.,*FEBS Lett.,* 30:291–295 (1973); Guillon et al., *J. Bacteriol.,* 174:4294–4301 (1992)). Consequently, levels of fVal-tRNA in vivo for the G34G36 mutant are quite low, approximately 20w. Overproduction of ValRS and MTF converted all of the G34G36 tRNA to fVal-tRNA and this accounts for the increased levels of CAT activity. (ii) With the G34 mutant initiator tRNA, which is aminoacylated with isoleucine, CAT activity in cells carrying this mutant tRNA is increased by overproduction of IF2 or MTF. Much of this tRNA is still uncharged. Therefore, overproduction of IleRS along with MTF could lead to substantial further increases in CT levels in vivo. (iii) With the U35A36 mutant tRNA, which is essentially all aminoacylated with glutamine and formylated in vivo, it is necessary to overproduce MetRS or IF2 for increased CAT protein synthesis. Our interpretation of the effect of overproduction of MetRS was that the fGln-tRNA was less active in initiation than fMet-tRNA and that overproduction of MetRS led to partial animoacylation of this tRNA with methionine, thereby converting it to a "more active" initiator tRNA. Similarly, the effect of overproduction of IF2 was attributed to fGln-tRNA being a poor substrate for binding to IF2. Overproduction of IF2 probably leads to increased binding of fGln-tRNA to IF2 and thereby to its increased utilization in initiation. Thus, several factors affect the synthesis in *E. coli* of CAT protein utilizing the mutant initiator tRNA. These include: (i) the extent of aminoacylation and formylation of the tRNA, (ii) the activity of the formylamincacylation tRNA in binding to IF2 and/or to the ribosome and (iii) the extent of overproduction of the mutant initiator tRNA. The importance of the third factor is underscored by the fact that the two mutant tRNAs used in this work produced much less of another reporter protein, dihydrofolate reductase, when cloned into a low copy vector (Pallanck and Schulman, *Proc. Natl. Acad. Sci., USA,* 88:3872–3876 (1991)). The dependence of CAT protein levels on levels of formylaminoacyl-tRNA in cells indicates strongly that initiation is the rate limiting step in translation of the CAT mRNA (Hershey, "Protein Synthesis", In Neidhart et al. (Eds.), *Escherichia coli and Salmonella Typhimurium, Cellular and Molecular Biology,* Amer. Soc. Microbiology, Washington, D.C., Chapter 40, pp. 613–647 (1987)).

Equivalents

Those skilled in the art will recognize, or be able to ascertain using no more than routine experimentation, many equivalents to the specific embodiments of the invention described herein. Such equivalents are intended to be encompassed by the following claims.

I claim:

1. A method of overproducing, in a prokaryotic host cell, a protein which is initiated with an amino acid other than methionine, comprising the steps of:
   a) introducing into the prokaryotic host cell;
      1) DNA which encodes the protein and which has an initiator codon for an amino acid other than methionine;
      2) DNA which encodes a mutant initiator tRNA containing the corresponding anti-codon; and
      3) DNA encoding methionyl-tRNA transformylase, thereby producing modified prokaryotic host cells; and
   b) maintaining the modified prokaryotic host cells under conditions appropriate for overproduction of the methionyl tRNA transformylase and expression of the DNA which encodes the protein and has an initiator codon for an amino acid other than methionine, wherein the protein which is initiated with an amino acid other than methionine is overproduced.

2. The method of claim 1 wherein the protein which is initiated with an amino acid other than methionine is initiated with valine, isoleucine or phenylalanine.

3. The method of claim 2 wherein the prokaryotic host cell is E. coli.

4. The method of claim 2 wherein the protein which is initiated with an amino acid other than methionine is hemoglobin or somatotropin.

5. The method of claim 1, further comprising in (a) introducing into the prokaryotic host cell DNA encoding the appropriate aminoacyl tRNA synthetase and in (b) maintaining the modified prokaryotic host cell under conditions appropriate for production of the appropriate aminoacyl tRNA synthetase.

6. A method of overproducing, in a prokaryotic host cell, a protein which is initiated with an amino acid other than methionine, comprising the steps of:
   a) introducing into the prokaryotic host cell:
      1) DNA which encodes the protein and which has an initiator codon for an amino acid other than methionine;
      2) DNA which encodes a mutant initiator tRNA containing the corresponding anti-codon;
      3) DNA encoding methionyl-tRNA transformylase;

4) DNA encoding the appropriate aminoacyl tRNA synthetase, thereby producing modified prokaryotic host cells; and b) maintaining modified prokaryotic host cells under conditions appropriate for overproduction of the methionyl-tRNA transformylase and the appropriae aminoacyl tRNA synthetase and expression of the DNA which encodes the protein and has an initiator codon for an amino acid other than methionine, wherein the protein which is initiated with an amino acid other than methionine is overproduced.

7. The method of claim 6 wherein the protein which is initiated with an amino acid other than methionine is initiated with valine, isoleucine or phenylalanine.

8. The method of claim 7 wherein the prokaryotic host cell is *E. coli*.

9. The method of claim 7 wherein the protein which is initiated with an amino acid other than methionine is hemoglobin or somatotropin.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( i i ) MOLECULE TYPE: tRNA ( x i ) SEQUENCE DESCRIPTION: SEQ ID NO:1:

CGCGGGGGGA GCAGCCUGGA GCUCGUCGGG CUCAUAACCC GAAGAUCGUC GGCAAAUCCG    60

GCCCCCGCAA CCA    73

( 2 ) INFORMATION FOR SEQ ID NO:2:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:2:

UUUCAGGAGC UAAGGAAGCU AAAAUGGACA AAAAAACCAC U    41

( 2 ) INFORMATION FOR SEQ ID NO:3:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear (  i  i  ) MOLECULE TYPE: RNA (genomic)

(  x  i  ) SEQUENCE DESCRIPTION: SEQ ID NO:3:

UUUCAGGAGC UAAGGAAGCU AAAGUCGACA AAAAAACCAC U                    41

( 2 ) INFORMATION FOR SEQ ID NO:4:

(  i  ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear (  i  i  ) MOLECULE TYPE: RNA (genomic)

(  x  i  ) SEQUENCE DESCRIPTION: SEQ ID NO:4:

UUUCAGGAGC UAAGGAAGCU AAAAUCGACA AAAAAACCAC U                    41

( 2 ) INFORMATION FOR SEQ ID NO:5:

(  i  ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:5:

CGGAATTCTG CGAAACAAGC TTTGCAGA                                   28

( 2 ) INFORMATION FOR SEQ ID NO:6:

(  i  ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (  i  i  ) MOLECULE TYPE: DNA (genomic)

(  x  i  ) SEQUENCE DESCRIPTION: SEQ ID NO:6:

ATGAATTCTT TACCATTTTG TATAAGAGA                                  29